(12) United States Patent
Saito et al.

(10) Patent No.: US 9,468,593 B2
(45) Date of Patent: Oct. 18, 2016

(54) ORAL COMPOSITION

(71) Applicant: KABUSHIKI KAISHA SANGI, Tokyo (JP)

(72) Inventors: Tomoki Saito, Tokyo (JP); Hiroyuki Kawamata, Tokyo (JP); Kazushi Ota, Tokyo (JP); Shuji Sakuma, Tokyo (JP)

(73) Assignee: Kabushiki Kaisha Sangi, Tokyo (JP)

( * ) Notice: Subject to any disclaimer, the term of this patent is extended or adjusted under 35 U.S.C. 154(b) by 0 days.

(21) Appl. No.: 14/425,537

(22) PCT Filed: Sep. 4, 2013

(86) PCT No.: PCT/JP2013/005231
§ 371 (c)(1),
(2) Date: Mar. 3, 2015

(87) PCT Pub. No.: WO2014/038195
PCT Pub. Date: Mar. 13, 2014

(65) Prior Publication Data
US 2015/0202128 A1    Jul. 23, 2015

(30) Foreign Application Priority Data

Sep. 5, 2012   (JP) ................. 2012-195044

(51) Int. Cl.
| | | |
|---|---|---|
| A61Q 11/00 | (2006.01) | |
| A61K 8/24 | (2006.01) | |
| A61K 9/14 | (2006.01) | |
| A61K 45/06 | (2006.01) | |
| A61K 8/18 | (2006.01) | |
| A61K 8/19 | (2006.01) | |

(52) U.S. Cl.
CPC . *A61K 8/24* (2013.01); *A61K 8/19* (2013.01); *A61Q 11/00* (2013.01); *A61K 2800/92* (2013.01)

(58) Field of Classification Search
CPC ............. A61Q 11/00; A61K 2300/00; A61K 2800/412; A61K 8/19; A61K 6/0085; A61K 8/24
See application file for complete search history.

(56) References Cited

U.S. PATENT DOCUMENTS

| | | | | |
|---|---|---|---|---|
| 4,081,526 A | * | 3/1978 | Asakawa ............... | A61Q 11/00 424/57 |
| 4,933,171 A | * | 6/1990 | Bristow .................. | A61K 8/19 424/49 |
| 2009/0186090 A1 | | 7/2009 | Zaidel et al. ................. | 424/489 |
| 2012/0027829 A1 | | 2/2012 | Hashimoto et al. .......... | 424/401 |
| 2012/0067748 A1 | | 3/2012 | Jung et al. ................... | 206/63.5 |

FOREIGN PATENT DOCUMENTS

| | | |
|---|---|---|
| CN | 103120623 | 5/2013 |
| JP | H08-175943 | 9/1996 |
| JP | H08-319224 | 12/1996 |
| JP | H09-249515 | 9/1997 |
| JP | H10-017449 | 1/1998 |
| JP | H10-265355 | 10/1998 |
| JP | H10-316547 | 12/1998 |
| JP | 2000-053547 | 2/2000 |
| JP | 2000-154126 | 6/2000 |
| JP | 2001-172146 | 6/2001 |
| JP | 2001-247456 | 9/2001 |
| JP | 2002-512177 | 4/2002 |
| JP | 2003-073246 | 3/2003 |
| JP | 2005-325102 | 11/2005 |

OTHER PUBLICATIONS

Simplestepsdental.com. Sensitive Teeth. Sep. 4, 2010. <http://www.simplestepsdental.com/SS/ihtSSPrint/r.==/st.32219/t.25019/pr.3/c.323744.html>. pp. 1-3.*
Kawamata, H. et al. "Potassium Nitrate Enhances Occlusion of Dentinal Tubules by Nano-Hydroxyapatite", Journal of Dental Research [online], vol. 87, 2008, p. 2265, [retrieved on Nov. 18, 2013], Retrieved from the Internet: <URL: http://www.sangi-co.com/vcms_1f/paper_o_200801.pdf>.
Kawamata, H. et al. "Investigation of Dentinal Surface Coating by Nano-hydroxyapatite" 88th General Session & Exhibition of the IADR [online], Jul. 2010, [retrieved on Nov. 18, 2013], Retrieved from the Internet: <URL: http://www.sangi-co.com/vcms_1f/paper_o_201002.pdf>.
Sangi Co., Ltd "New Research Results Report on Hyperesthesia Suppression—Chikaku Kabin Yokusei ni Kansuru Atarashii Kenkyu Seika Happyo" [online], Jul. 2008, pp. 1 to 5, [retrieved on Nov. 18, 2013], Retrieved from the Internet: <URL: http://www.sangi-co.com/vcms_1f/sangi20080704-.pdf5> (Japanese with English Summary).
Sangi Co., Ltd. "New Research Results of Dental Component Nano-Hydroxyapatite-Shikayo Seibun Nano Ryushi Hydroxyapatite no Atarashii Kenkyu Seika", [online] Jul. 2010, pp. 1 to 7, [retrieved on Nov. 18, 2013], Retrieved from the Internet: <URL: http://www.sangi-co.com/vcms_1f/release20100715.pdf> (Japanese with English Summary).
Translation of International Preliminary Report on Patentability for PCT/JP2013/005231 issued on Mar. 19, 2015.
Extended European Search Report Issued in Corresponding European Patent Application No. 13835202.6, dated May 17, 2016.
Komabayashi et al., "Dentin permeability reduction by a sequential application of calcium and fluoride-phosphate solutions", *Journal of Dentistry*, 38: 736-741, 2010.
Wang Zhe-Jun et al., "The mechanism and effect of treating dentine hypersensitivity by dentinal tubule occlusion", vol. 37, Term 1, pp. 81-84, Jan. 2010. (English abstract and partial translation provided).
Office Action issued in Chinese Patent Application No. 201380054503.0, dated May 4, 2016. (Partial Translation provided).

* cited by examiner

*Primary Examiner* — Frederick Krass
*Assistant Examiner* — Tracy Liu
(74) *Attorney, Agent, or Firm* — Norton Rose Fulbright US LLP

(57) ABSTRACT

The present invention provides an oral composition comprising hydroxyapatite, potassium nitrate, and calcium monohydrogen phosphate, wherein the composition has an increased ability to occlude dentinal tubules of a tooth and has an excellent inhibitory effect on hypersensitivity.

1 Claim, 8 Drawing Sheets

ORAL COMPOSITION

This application is a national phase application under 35 U.S.C. §371 of International Application No. PCT/JP2013/005231, filed Sep. 4, 2013, which claims priority to Japanese Patent Application No. 2012-195044, filed Sep. 5, 2012, the entire contents of each of which are incorporated herein by reference.

TECHNICAL FIELD

The present invention relates to oral compositions that promote occlusion of a dentinal tubule of a tooth to inhibit hypersensitivity.

BACKGROUND ART

When having cold or hot stuff and/or sweet or sour stuff in the mouth, people sometimes feel acute electrical tooth pain. This is generally called hypersensitivity, and this occurs when gums become thinner due to, for example, periodontitis and the dentin of a tooth root is then exposed and/or when enamel is damaged and the dentin is then exposed. Accordingly, this is also called dentin hypersensitivity. This dentin hypersensitivity is believed to occur when dentinal tubules on the surface of dentin have openings and physical and chemical stimulation such as brushing and/or temperature stimulation is given to the openings. However, there have been various theories on the mechanism of its onset and the mechanism is thus not fully understood. Nowadays, the "hydrodynamic theory," in which brushing and/or temperature stimulation, for example, is given and the internal fluid of dentinal tubules then moves, seems to be plausible.

In addition, during bleaching treatment so as to effectively achieve beautiful appearance, there is a concern about the hypersensitivity problem. Hence, a method for inhibiting dentin hypersensitivity has been sought.

Some dentinal tubule occlusion methods, one means for inhibiting the dentin hypersensitivity, have been proposed, including: for example, a method (Patent Document 1) using a dental therapeutic agent for hypersensitivity, the agent comprising an acidulated phosphate fluoride-tannic acid solution component, a lanthanum chloride aqueous solution component, and fluoroapatite-based glass powder; and a method (Patent Document 2) using a therapeutic agent for dentin hypersensitivity, the agent consisting of an oxalic acid compound solution and a calcium compound solution. Other dentinal tubule occlusion methods using hydroxyapatite have also been proposed, including: a method (Patent Document 3) using a composition for hypersensitivity, the composition using hydroxyapatite with a particle size of from 1.0 μm to 5.0 μm; and a method (Patent Document 4) using a sealant for dentinal tubules while sintered hydroxyapatite particles with a particle size of 900 nm or less are used for the dentinal tubule sealant.

Further, the following has been proposed, including: a hypersensitivity-inhibiting dentifrice (Patent Document 5) comprising potassium nitrate and stannous fluoride as an oral composition using potassium nitrate that functions as an agent for alleviating and inhibiting hypersensitivity; an oral composition (Patent Document 6) in which amino acid and a salt thereof or nucleic acid and a salt thereof are blended in an oral composition comprising potassium nitrate; an oral composition (Patent Document 7) comprising specific concentrations of a potassium salt and an aluminum salt; and an oral composition (Patent Document 8) in which potassium nitrate and reduced palatinose are blended.

Meanwhile, calcium monohydrogen phosphate dihydrate (dibasic calcium phosphate) is used as, for example, a base material for dentifrice, a cleaning agent, or a polishing agent. Some oral compositions using calcium monohydrogen phosphate dihydrate have been proposed, including: for example, in order to remove plaques on the surface of a tooth to increase whiteness of the tooth, a dentifrice composition (Patent Document 9) comprising aggregated particles selected from calcium carbonate, dibasic calcium phosphate, tribasic calcium phosphate, calcium pyrophosphate, and hydroxyapatite, the particles having an average particle size of 3.5 to 10 μm and a disintegration strength of 0.1 to 5 g/particle; and in order to effectively remove tooth colorants without significantly damaging a tooth, a dentifrice composition (Patent Document 10) comprising: granules having an average particle size of 100 to 500 μm and a disintegration strength of 0.1 to 10 g/granule, the granules being prepared using powder as a polishing agent such as dibasic calcium phosphate, tribasic calcium phosphate, calcium pyrophosphate, magnesium phosphate, insoluble sodium metaphosphate, silica, hydroxyapatite, aluminum hydroxide, alumina, calcium carbonate, magnesium carbonate, calcium sulfate, zeolite, an aluminosilicate complex, and red iron oxide; and at least one polishing powder selected from zeolite, calcium carbonate, dibasic calcium phosphate anhydride, tribasic calcium phosphate, hydroxyapatite, and aluminum hydroxide, the powder particles having a Mohs' hardness of 2 to 6 and an average particle size of 0.5 to 5 μm.

PRIOR ART DOCUMENTS

Patent Documents

Patent Document 1: Japanese unexamined Patent Application Publication No. 09-249515
Patent Document 2: Japanese unexamined Patent Application Publication No. 2001-247456
Patent Document 3: Japanese unexamined Patent Application Publication No. 10-17449
Patent Document 4: Japanese unexamined Patent Application Publication No. 2005-325102
Patent Document 5: Japanese unexamined Patent Application Publication (Translation of PCT Application) No. 2002-512177
Patent Document 6: Japanese unexamined Patent Application Publication No. 08-175943
Patent Document 7: Japanese unexamined Patent Application Publication No. 2001-172146
Patent Document 8: Japanese unexamined Patent Application Publication No. 2003-73246
Patent Document 9: Japanese unexamined Patent Application Publication No. 2000-154126
Patent Document 10: Japanese unexamined Patent Application Publication No. 10-316547

SUMMARY OF THE INVENTION

Object to be Solved by the Invention

It is an object of the present invention to provide an oral composition that has an increased ability to occlude dentinal tubules of a tooth and has an excellent inhibitory effect on hypersensitivity.

Means to Solve the Object

The present inventors have conducted intensive research so as to solve the above object and have found that simultaneously blending hydroxyapatite, which has been known to have an ability to occlude dentinal tubules of a tooth, with calcium monohydrogen phosphate and potassium nitrate, which has not been known to have the ability to occlude dentinal tubules of a tooth, results in an unexpected increase in occlusion of the dentinal tubules of a tooth. Then, the present invention has been completed. The present inventors have found an unexpected effect in which: potassium nitrate, in particular, does not have an ability to occlude dentinal tubules of a tooth when used alone and does not exhibit a particular effect when mixed with either hydroxyapatite or calcium monohydrogen phosphate; and potassium nitrate, however, can markedly increase the ability to occlude dentinal tubules of a tooth when combined with both hydroxyapatite and calcium monohydrogen phosphate.

Specifically, the present invention relates to: (1) an oral composition having an ability to occlude a dentinal tubule of a tooth, the composition comprising hydroxyapatite, potassium nitrate, and calcium monohydrogen phosphate; (2) the oral composition according to (1), wherein the calcium monohydrogen phosphate is calcium monohydrogen phosphate dihydrate; (3) the oral composition according to the above (1) or (2), wherein an amount of hydroxyapatite in the composition is 0.5 to 20% by weight; (4) the oral composition according to any one of the above (1) to (3) wherein an amount of potassium nitrate in the composition is 2.5 to 10% by weight; and (5) the oral composition according to any one of the above (1) to (4), wherein an amount of calcium monohydrogen phosphate in the composition is 0.5 to 25% by weight in calcium monohydrogen phosphate dihydrate equivalent.

Effect of the Invention

An oral composition according to the present invention is an oral composition comprising three components of hydroxyapatite, potassium nitrate, and calcium monohydrogen phosphate as active ingredients. The oral composition has an increased ability to occlude dentinal tubules and is very effective in inhibiting hypersensitivity.

MODE FOR CARRYING OUT THE INVENTION

Figure 1:
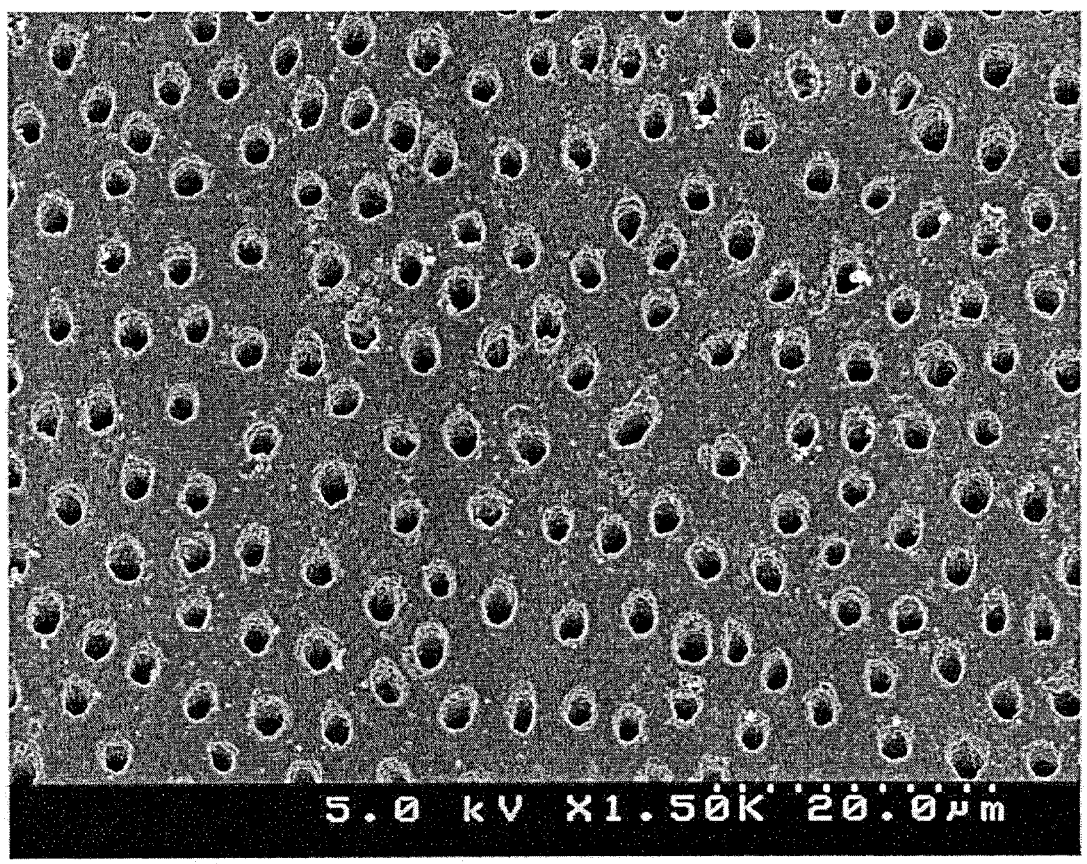
FIG. 1 is a photograph showing an untreated dentin surface.
Figure 2:
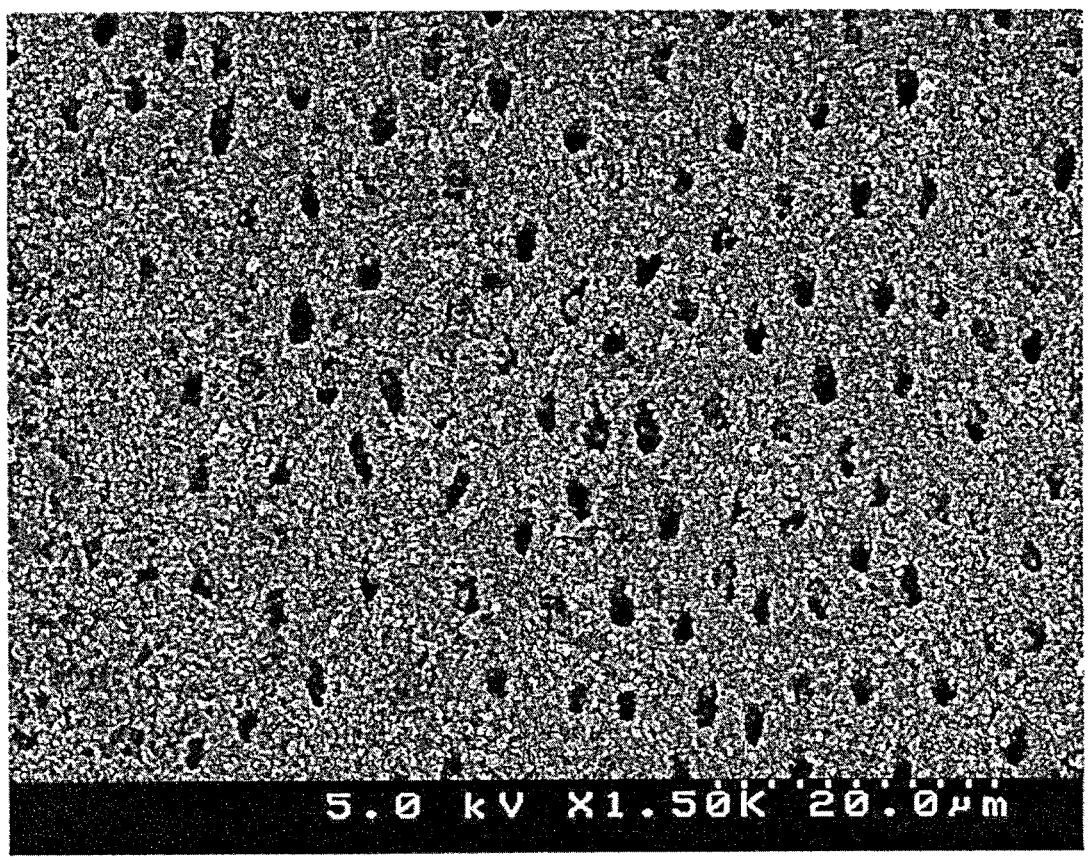
FIG. 2 is a photograph showing a dentin surface after soaking treatment according to Example 15.
Figure 3:
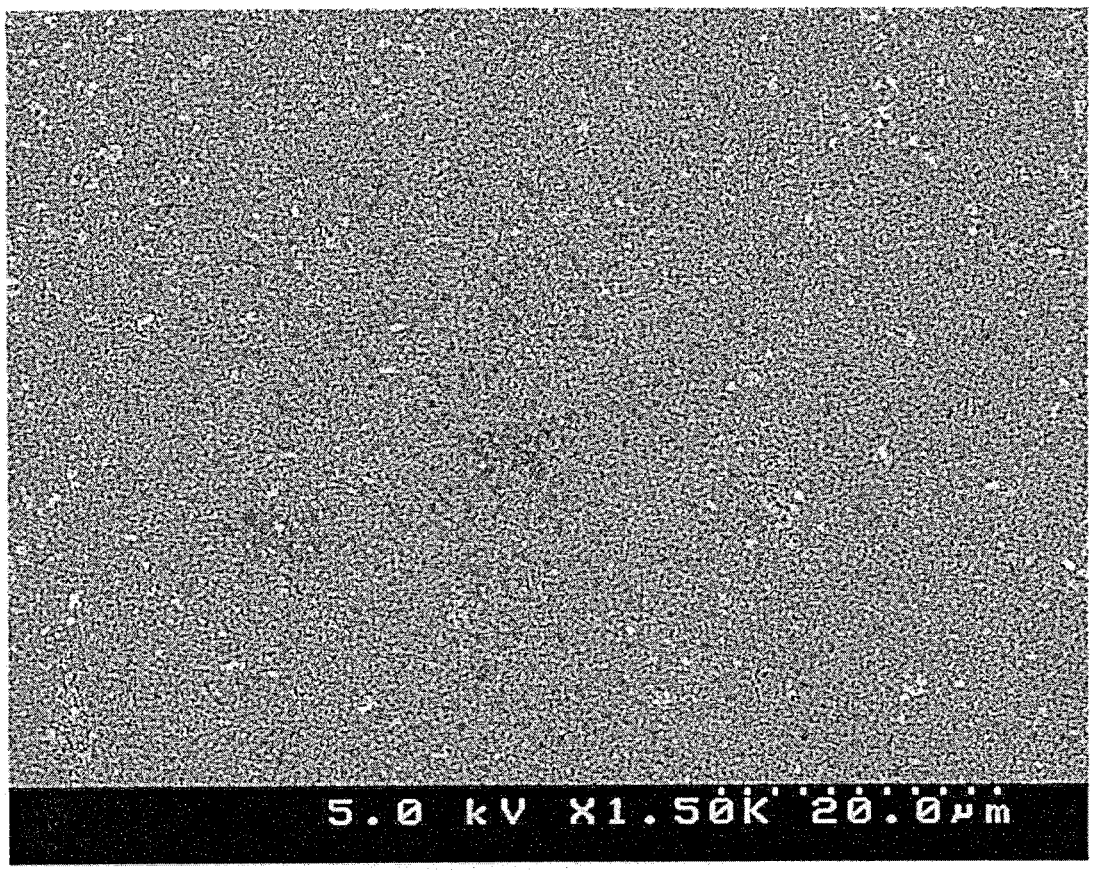
FIG. 3 is a photograph showing a dentin surface after soaking treatment according to Example 30.
Figure 4:
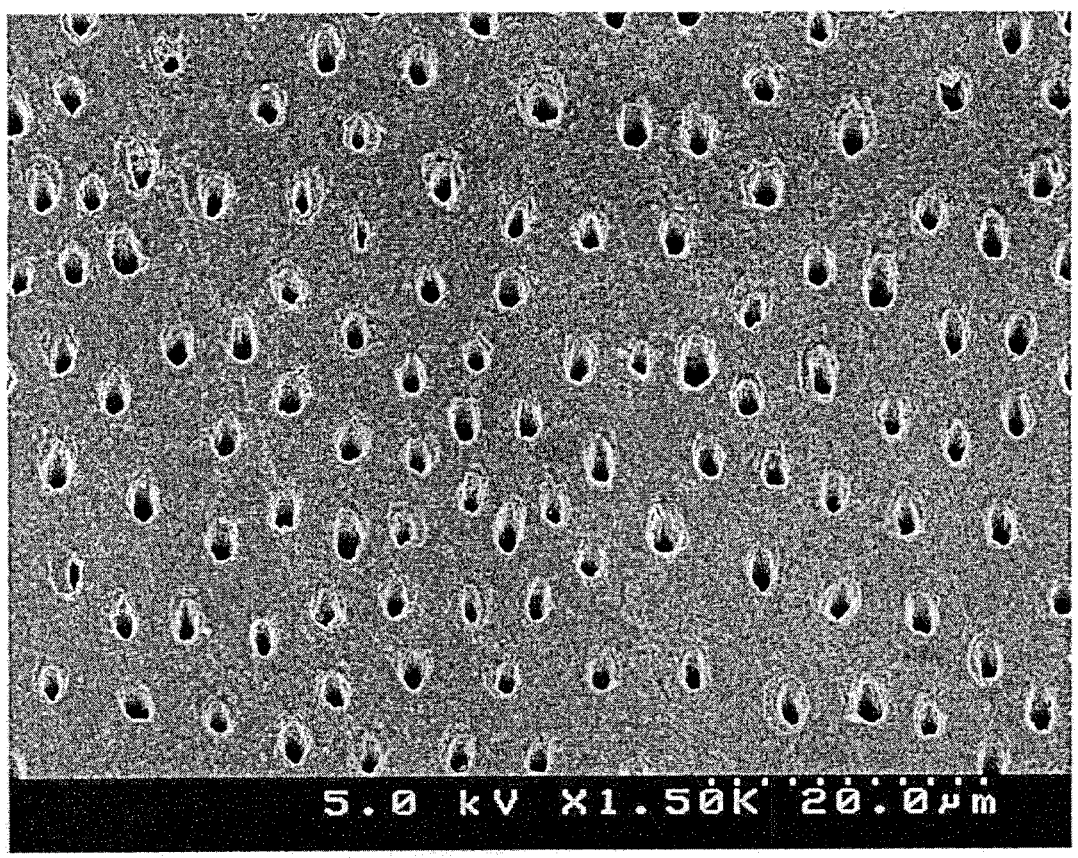
FIG. 4 is a photograph showing a dentin surface after soaking treatment according to Comparative Example 11.
Figure 5:
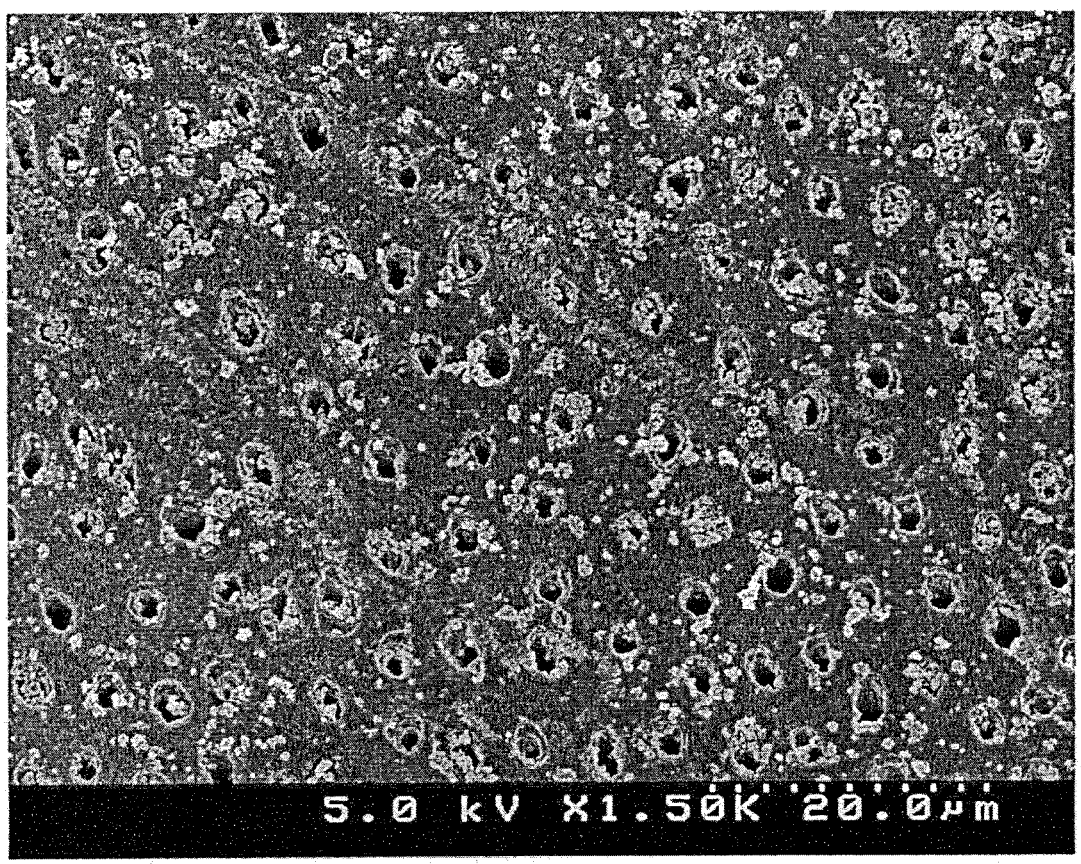
FIG. 5 is a photograph showing a dentin surface after soaking treatment according to Comparative Example 30.
Figure 6:
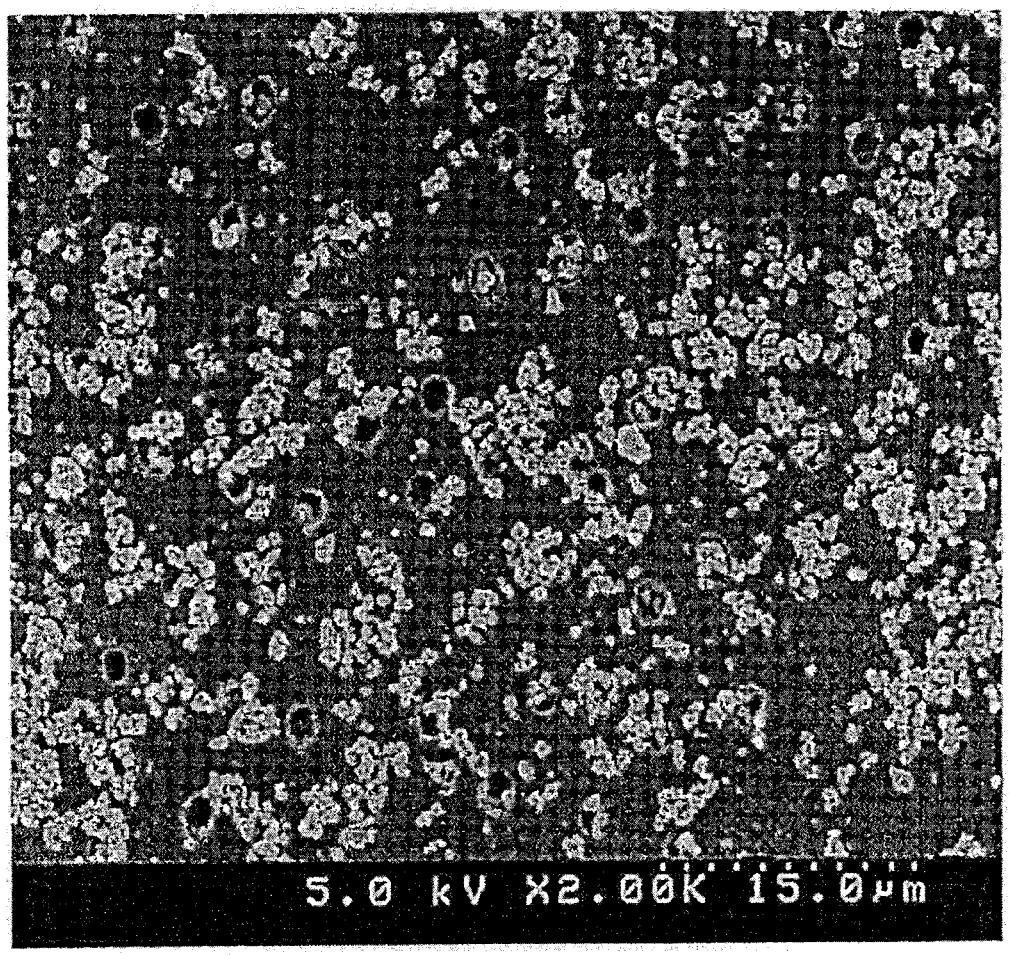
FIG. 6 is a photograph showing a dentin surface after soaking treatment according to Comparative Example 31.
Figure 7:
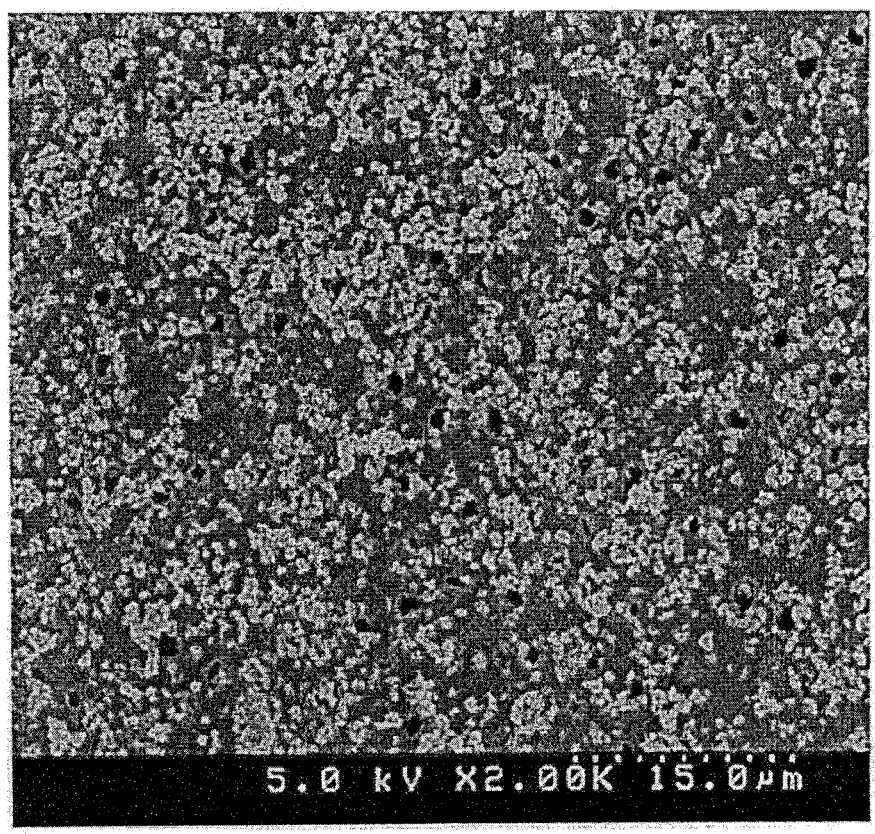
FIG. 7 is a photograph showing a dentin surface after soaking treatment according to Comparative Example 43.

An oral composition having an ability to occlude dentinal tubules of a tooth according to the present invention is not particularly limited as long as the composition contains hydroxyapatite, potassium nitrate, and calcium monohydrogen phosphate. As a form of the oral composition according to the present invention, any form may be employed, including a solid, solidified product, liquid, fluid, gel, paste, and gum. Specific examples include: a dentifrice such as a toothpaste, a liquid dentifrice, a fluid dentifrice, and a tooth semi-paste; a mouthwash; and an ointment.

An oral composition according to the present invention exerts the unexpected effect of synergistically increasing an occlusion rate of dentinal tubules of a tooth by including three components of hydroxyapatite, potassium nitrate, and calcium monohydrogen phosphate. That is, although any two components of these three components are mixed, no effect of synergistically increasing the occlusion rate of dentinal tubules is observed. However, once all the three components are blended, the effect of synergistically increasing the occlusion rate of dentinal tubules of a tooth can be recognized (see Examples for details).

Hydroxyapatite used in the present invention is a kind of calcium phosphate. The hydroxyapatite may be those synthesized using a common procedure or may be those obtained as a natural hard tissue from, for example, a fish bone of food fish such as a salmon, a pork bone, and a bovine bone. Hydroxyapatite usually has a stoichiometric composition of $Ca_{10}(PO_4)_6(OH)_2$. Even if the Ca/P molar ratio is non-stoichiometric and is not 1.67, the hydroxyapatite exhibits its own specific characteristics and can have an apatite structure. For example, synthetic hydroxyapatite having a Ca/P molar ratio of about 1.4 to 1.8 is included in the hydroxyapatite according to the present invention.

The hydroxyapatite used in the present invention may be any of crystalline, low crystalline, or amorphous ones. In view of a dental caries prevention effect, it is preferable to use low crystalline or amorphous hydroxyapatite (hereinafter, the low crystalline hydroxyapatite and the amorphous hydroxyapatite are referred to as "amorphous hydroxyapatite"). Note that the term "low crystalline" refers to a state in which a crystalline substance has a broader X-ray diffraction peak than high crystalline powder. The term "amorphous" refers to a state in which a substance exhibits a broad harrow in an X-ray diffraction pattern and no crystal-specific diffraction pattern. Such amorphous hydroxyapatite can be obtained by, for example, subjecting apatite synthesized using a wet synthesis method to lyophilization or drying at a temperature of 100° C. or lower or by firing the apatite at a temperature of about 300° C. or lower.

The hydroxyapatite according to the present invention may be usually used as powder or in a water suspension state. The hydroxyapatite has a maximum particle size of preferably 100 µm or less as measured using a laser diffraction/scattering particle size distribution analyzer (LA-950, manufactured by Horiba, Ltd.). The lower limit of the particle size is about 0.001 µm in view of production. In addition, the average particle size is preferably from 0.01 to 10 µm and more preferably from 0.05 to 5 µm. Note that the hydroxyapatite has a specific surface area of about 100 $m^2/g$ or less as measured using a BET method. In addition, depending on the need, the hydroxyapatite can be made into powder, followed by subjecting the powder to drying and by making the resulting powder porous and electrostatic, etc., for usage.

A larger amount of hydroxyapatite in an oral composition according to the present invention is preferable in view of increasing occlusion of dentinal tubules of a tooth. When a formulation viewpoint such as viscosity is taken into consideration, the amount blended is preferably from 0.5 to 20% by weight, more preferably from 1 to 10% by weight, and still more preferably from 5 to 10% by weight. Hydroxyapatite has been previously known to have the action of occluding dentinal tubules of a tooth. As described above, in view of increasing the occlusion of dentinal tubules of a tooth, a larger amount blended is preferable. However, according to the present invention, a combination of hydroxyapatite with potassium nitrate and calcium monohydrogen phosphate can synergistically increase the above effect. Hence, this makes it possible to decrease a usage amount of expensive hydroxyapatite.

The potassium nitrate used in the present invention is a kind of nitrate represented by a chemical formula: $KNO_3$. Examples of the potassium nitrate that can be used include any of a food additive, a first grade reagent, and a special grade reagent. This potassium nitrate exerts an effect in which ionized potassium inhibits neural transmission to alleviate pain caused by hypersensitivity. Nowadays, this potassium nitrate has been used for a dentifrice for hypersensitivity, but has no ability to occlude dentinal tubules of a tooth (see Comparative Examples 8 to 11). However, according to the present invention, a combination of this potassium nitrate with both hydroxyapatite and calcium monohydrogen phosphate is used to exert the unexpected effect of markedly increasing occlusion of dentinal tubules of a tooth.

In view of increasing occlusion of dentinal tubules of a tooth, a larger amount of potassium nitrate in an oral composition according to the present invention is preferable. When a formulation viewpoint such as viscosity is taken into consideration, the amount blended is preferably from 2.5 to 10% by weight and more preferably from 5 to 10% by weight.

The calcium monohydrogen phosphate used in the present invention is a kind of calcium phosphate represented by a chemical formula: $CaHPO_4$. The calcium monohydrogen phosphate may be an anhydride or a hydrate. In view of moisture absorption and stability, the calcium monohydrogen phosphate is preferably calcium monohydrogen phosphate dihydrate (DCPD) represented by a chemical formula: $CaHPO_4 \cdot 2H_2O$. Calcium monohydrogen phosphate dihydrate has been widely used as a pharmaceutical excipient, a calcium enhancer, a base material for dentifrice, a feed additive, a synthetic resin modifier, a glaze raw material, or a ceramic raw material. Examples of the calcium monohydrogen phosphate dihydrate used in the present invention may include any kind described in the Japanese Standards of Food Additives, the Japanese Pharmacopoeia, the Japanese Standards of Quasi-drug Ingredients 2006, and the like. In addition, in the case of using, for example, anhydrous calcium phosphate as calcium monohydrogen phosphate, stable calcium monohydrogen phosphate dihydrate is present during adjustment and usage of an oral composition according to the present invention because the anhydrous calcium phosphate is hygroscopic.

In view of increasing occlusion of dentinal tubules of a tooth, a larger amount of calcium monohydrogen phosphate blended in an oral composition according to the present invention is preferable. When a formulation viewpoint such as viscosity is taken into consideration, the amount blended is preferably from 0.5 to 25% by weight in calcium monohydrogen phosphate dehydrate equivalent, more preferably from 1 to 20% by weight, and still more preferably from 5 to 20% by weight. The present invention reveals that even calcium monohydrogen phosphate dihydrate alone has an ability to occlude dentinal tubules of a tooth and contributes to occlusion of the dentinal tubules (see Comparative Examples 12 to 17). However, when the calcium monohydrogen phosphate dihydrate is combined with both hydroxyapatite and potassium nitrate, their occlusion can be markedly enhanced.

In addition, in order to achieve a markedly high occlusion ability, an oral composition according to the present invention preferably contains a large amount of hydroxyapatite compared with calcium monohydrogen phosphate. In order to economically achieve a predetermined high occlusion ability, the composition preferably contains a large amount of calcium monohydrogen phosphate compared with hydroxyapatite.

An oral composition according to the present invention can contain, in addition to the above-described three essential components, various components such as an additive, a moisturizer, a foaming agent, a flavoring agent, a sweetener, and a preservative that can be usually used in the oral composition. The following describes specific examples of these components. Note that components that can be blended in an oral composition according to the present invention are not limited to these components.

Examples of a polishing agent include calcium phosphate, tribasic calcium phosphate, calcium carbonate, calcium pyrophosphate, silica such as polishing precipitated silica and polishing gel silica, calcium silicate, aluminum silicate, aluminum oxide, aluminum hydroxide, alumina, zeolite, titanium oxide, zirconium silicate, insoluble sodium metaphosphate, tribasic magnesium phosphate, magnesium carbonate, calcium sulfate, magnesium sulfate, methyl polymethacrylate, bentonite, and a synthetic resin.

Examples of the moisturizer include polyhydric alcohol such as glycerin, propylene glycol, polyethylene glycol, sorbitol, xylitol, ethylene glycol, 1,3-butylene glycol, and isopropylene glycol.

Examples of the foaming agent include sodium lauryl sulfate, an N-lauroylsarcosine sodium salt, and a nonionic surfactant.

Examples of a thickener include hydroxyethyl cellulose, sodium carboxymethyl cellulose, carrageenan, a carboxyvinyl polymer, xanthan gum, gelatin, pullulan, sodium alginate, sodium polyacrylate, polyvinyl alcohol, locust bean gum, guar gum, and hydroxypropyl methylcellulose.

Examples of a binder include methyl cellulose, propylene glycol alginate, pullulan, tragacanth gum, xanthan gum, pectin, furcellaran, chitosan, polyethylene oxide, polyvinylpyrrolidone, polyacrylic acid, polymethacrylic acid, peptone, casein, collagen, albumin, gum arabic, karaya gum, eudragit, ethyl cellulose, cellulose acetate, sodium polyacrylate, polyvinyl alcohol, polyvinyl acetal·dimethylamino acetate, and cellulose acetate·dibutylhydroxypropyl ether.

Examples of an emulsifier include polyoxyethylene hydrogenated castor oil, sorbitan monostearate, glycerin fatty acid ester, propyleneglycol fatty acid ester, alkyl glyceryl ether, polyoxyethylene sorbitol fatty acid ester, polysorbate, polyoxyethylene, lauromacrogol, sodium alkyl sulfate, alkyl phosphate, sodium alkyl benzene sulfonate, sodium N-acyl sarcosinate, N-acyl glutamate, sucrose fatty acid ester, alkyl glycosides, alkyldimethylamine oxide, and alkyl betaines.

Examples of a fat and oil component include liquid paraffin, paraffin, higher alcohol such as cetyl alcohol and stearyl alcohol, fatty acid ester such as isopropyl myristate, lanolin, whale wax, carnauba wax, fatty acids, an ester compound such as octyl dodecyl myristate, diisopyl adipate, hexadecyl isostearate, and decyl oleate, squalane, squalene, medium chain fatty acid triglyceride, and silicon.

Examples of alcohol include: lower alcohol such as ethanol, propyl alcohol, isopropyl alcohol, butanol, and isobutanol; and polyhydric alcohol such as ethylene glycol, diethylene glycol, propylene glycol, dipropylene glycol, 1,3-butylene glycol, glycerin, 1,5-pentadiol, sorbitol, and polyethylene glycol.

Examples of a surfactant are listed as follows. Examples of a nonionic surfactant include sorbitan fatty acid ester, glycerin fatty acid ester, decaglycerin fatty acid ester, polyglycerin fatty acid ester, propylene glycol•pentaerythritol fatty acid ester, polyoxyethylene sorbitan fatty acid ester, polyoxyethylene glycerin fatty acid ester, polyoxyethylene sorbitol fatty acid ester, polyethylene glycol fatty acid ester, polyoxyethylene alkylether, polyoxyethylene polyoxypropylene glycol, polyoxypropylene alkylether, polyoxyethylene polyoxypropylene alkylether, polyoxyethylene alkylphenyl ether, polyoxyethylene castor oil•hydrogenated castor oil, a polyoxyethylene lanolin•lanolin alcohol•bees wax derivative, polyoxyethylene alkylamine•fatty acid amide, a polyoxyethylene alkylphenyl formaldehyde condensate, and single chain length polyoxyethylene alkylether. Examples of an anionic surfactant include sodium lauryl sulfate, sodium myristyl sulfate, alkyl sulfate, polyoxyethylene alkyl sulfate, N-acyl amino acid and a salt thereof, N-acyl methyl taurine and a salt thereof, polyoxyethylene alkylether acetate, alkyl sulfocarboxylate, α-olefin sulfonate, alkyl phosphate, and polyoxyethylene alkylether phosphate. Examples of a cationic surfactant include alkyl ammonium, and an alkylbenzyl ammonium salt. Examples of an amphoteric surfactant include betaine acetate, imidazolinium betaine, and lecithin. Examples of the nonionic surfactant further include sucrose fatty acid ester and decaglyceryl laurate.

Examples of a pH modifier include citric acid and a salt thereof, phosphoric acid and a salt thereof, malic acid and a salt thereof, gluconic acid and a salt thereof, maleic acid and a salt thereof, aspartic acid and a salt thereof, gluconic acid and a salt thereof, succinic acid and a salt thereof, glucuronic acid and a salt thereof, fumaric acid and a salt thereof, glutamic acid and a salt thereof, adipic acid and a salt thereof, inorganic acid such as hydrochloric acid, hydrofluoric acid, alkali metal hydroxide such as sodium hydroxide and potassium hydroxide, and amines such as triethanolamine, diethanolamine, and diisopropanolamine.

Examples of the preservative include paraoxybenzoate, alkyldiaminoethylglycine hydrochloride, methylparaben, ethylparaben, and sodium benzoate.

Examples of a stabilizer include sodium sulfite, sodium hydrogen sulfite, dibutylhydroxy toluene, butylhydroxyanisole, and edetic acid or salts thereof.

Examples of the flavoring agent include menthol, essential oil from peppermint or spearmint, eucalyptus oil, orange oil, lemon oil, wintergreen oil, clove oil, Japanese peppermint oil, thyme oil, sage oil, carvone, linalool, eugenol, anethole, and herb mint.

Examples of the stabilizer further include vitamin C, vitamin E, and a derivative thereof, sodium sulfite, sodium pyrosulfite, sodium hydrogen sulfite, butyl hydroxy toluene, and butylhydroxyanisole.

Examples of the sweetener include saccharin sodium, aspartame, stevioside, neohesperidin dihydrochalcone, glycyrrhizin, aspartylphenyl alanine methyl ester, acesulfame potassium, perillatin, p-methoxy cinnamic aldehyde, and xylitol.

Examples of other medicinal ingredients include allantoin, tocopherol acetate, isopropylphenol, triclosan, chlorhexidine, chlorophyll, flavonoid, tranexamic acid, hinokitiol, cetylpyridinium chloride, sodium fluoride, stannous fluoride, sodium monofluorophosphate, dextranase, mutanase, protease, aminocaproic acid, glycyrrhizic acid, glycyrrhetic acids, azulene, allantoin, lysozyme chloride, *Hordeum sativum* extract, polyphosphoric acids, and sodium chloride.

Note that an amount of each of these optional components blended is suitably used within a pharmacologically acceptable range without hindering the effects of the present invention. In addition, it may be possible to add hydroxyapatite, potassium nitrate, calcium monohydrogen phosphate, and the other optional components in any step during the production of an oral composition according to the present invention.

EXAMPLES

Example 1

The following details the present invention with reference to Examples. The technical scope of the present invention, however, is not limited to the following Examples.

Production of Hydroxyapatite

First, a phosphoric acid aqueous solution having a concentration of 30% by mass was dropwise added to a calcium hydroxide suspension under stirring until a pH became 10. Produced gelatinous substance was left and matured at room temperature for 1 day. Next, the gelatinous substance was filtered with a glass filter. Then the residue was dried in the air at 100° C. to yield hydroxyapatite powder. The resulting hydroxyapatite powder had a maximum particle size of about 40 μm, a minimum particle size of about 0.05 μm, and an average particle size of about 5 μm.

Potassium Nitrate

A special grade reagent, manufactured by Wako Pure Chemical Industries, Ltd., was used as potassium nitrate.

Calcium Monohydrogen Phosphate Dihydrate

A raw material standard 2006, a quasi-medicine, manufactured by Taihei Chemical Industrial Co., Ltd., was used as calcium monohydrogen phosphate dihydrate.

Preparation of Oral Compositions According to Examples and Comparative Examples

Toothpastes, mouthwashes, and dentinal tubule-occluding agents having the following compositions were manufactured according to a common procedure, and a dentinal tubule occlusion test was conducted.

TABLE 1

| | Toothpastes | | | | | |
|---|---|---|---|---|---|---|
| | Example 1 | Example 2 | Example 3 | Example 4 | Example 5 | Example 6 |
| Hydroxyapatite | 0.5 | 0.5 | 0.5 | 0.5 | 0.5 | 0.5 |
| Potassium nitrate | 2.5 | 2.5 | 5.0 | 5.0 | 10.0 | 10.0 |
| Calcium monohydrogen | 0.5 | 25.0 | 5.0 | 20.0 | 0.5 | 25.0 |

TABLE 1-continued

| Toothpastes | Example 1 | Example 2 | Example 3 | Example 4 | Example 5 | Example 6 |
|---|---|---|---|---|---|---|
| phosphate dihydrate | | | | | | |
| Glycerin | 20.0 | 20.0 | 20.0 | 20.0 | 20.0 | 20.0 |
| Polyethylene glycol | 3.0 | 3.0 | 3.0 | 3.0 | 3.0 | 3.0 |
| Sodium lauryl sulfate | 1.0 | 1.0 | 1.0 | 1.0 | 1.0 | 1.0 |
| Xanthan gum | 0.5 | 0.5 | 0.5 | 0.5 | 0.5 | 0.5 |
| Hydroxyethyl cellulose | 0.5 | 0.5 | 0.5 | 0.5 | 0.5 | 0.5 |
| Menthol | 0.5 | 0.5 | 0.5 | 0.5 | 0.5 | 0.5 |
| Purified water | balancer | balance | balance | balance | balance | balance |
| Total | 100.0 | 100.0 | 100.0 | 100.0 | 100.0 | 100.0 |

TABLE 2

| Toothpastes | Example 7 | Example 8 | Example 9 | Example 10 | Example 11 | Example 12 |
|---|---|---|---|---|---|---|
| Hydroxyapatite | 1.0 | 1.0 | 1.0 | 1.0 | 1.0 | 1.0 |
| Potassium nitrate | 2.5 | 2.5 | 5.0 | 5.0 | 10.0 | 10.0 |
| Calcium monohydrogen phosphate dihydrate | 0.5 | 25.0 | 5.0 | 10.0 | 0.5 | 25.0 |
| Glycerin | 20.0 | 20.0 | 20.0 | 20.0 | 20.0 | 20.0 |
| Polyethylene glycol | 3.0 | 3.0 | 3.0 | 3.0 | 3.0 | 3.0 |
| Sodium lauryl sulfate | 1.0 | 1.0 | 1.0 | 1.0 | 1.0 | 1.0 |
| Xanthan gum | 0.5 | 0.5 | 0.5 | 0.5 | 0.5 | 0.5 |
| Hydroxyethyl cellulose | 0.5 | 0.5 | 0.5 | 0.5 | 0.5 | 0.5 |
| Menthol | 0.5 | 0.5 | 0.5 | 0.5 | 0.5 | 0.5 |
| Purified water | balance | balance | balance | balance | balance | balance |
| Total | 100.0 | 100.0 | 100.0 | 100.0 | 100.0 | 100.0 |

TABLE 3

| Toothpastes | Example 13 | Example 14 | Example 15 | Example 16 | Example 17 | Example 18 |
|---|---|---|---|---|---|---|
| Hydroxyapatite | 5.0 | 5.0 | 5.0 | 5.0 | 5.0 | 5.0 |
| Potassium nitrate | 2.5 | 2.5 | 5.0 | 7.5 | 10.0 | 10.0 |
| Calcium monohydrogen phosphatedihydrate | 0.5 | 25.0 | 10.0 | 10.0 | 0.5 | 25.0 |
| Glycerin | 20.0 | 20.0 | 20.0 | 20.0 | 20.0 | 20.0 |
| Polyethylene glycol | 3.0 | 3.0 | 3.0 | 3.0 | 3.0 | 3.0 |
| Sodium lauryl sulfate | 1.0 | 1.0 | 1.0 | 1.0 | 1.0 | 1.0 |
| Xanthan gum | 0.5 | 0.5 | 0.5 | 0.5 | 0.5 | 0.5 |
| Hydroxyethyl cellulose | 0.5 | 0.5 | 0.5 | 0.5 | 0.5 | 0.5 |
| Menthol | 0.5 | 0.5 | 0.5 | 0.5 | 0.5 | 0.5 |
| Purified water | balance | balance | balance | balance | balance | balance |
| Total | 100.0 | 100.0 | 100.0 | 100.0 | 100.0 | 100.0 |

TABLE 4

| Toothpastes | Example 19 | Example 20 | Example 21 | Example 22 | Example 23 | Example 24 |
|---|---|---|---|---|---|---|
| Hydroxyapatite | 10.0 | 10.0 | 10.0 | 10.0 | 10.0 | 10.0 |
| Potassium nitrate | 2.5 | 2.5 | 5.0 | 7.5 | 10.0 | 10.0 |

TABLE 4-continued

| | Toothpastes | | | | | |
|---|---|---|---|---|---|---|
| | Example 19 | Example 20 | Example 21 | Example 22 | Example 23 | Example 24 |
| Calcium monohydrogen phosphatedihydrate | 0.5 | 25.0 | 1.0 | 20.0 | 0.5 | 25.0 |
| Glycerin | 20.0 | 20.0 | 20.0 | 20.0 | 20.0 | 20.0 |
| Polyethylene glycol | 3.0 | 3.0 | 3.0 | 3.0 | 3.0 | 3.0 |
| Sodium lauryl sulfate | 1.0 | 1.0 | 1.0 | 1.0 | 1.0 | 1.0 |
| Xanthan gum | 0.5 | 0.5 | 0.5 | 0.5 | 0.5 | 0.5 |
| Hydroxyethyl cellulose | 0.5 | 0.5 | 0.5 | 0.5 | 0.5 | 0.5 |
| Menthol | 0.5 | 0.5 | 0.5 | 0.5 | 0.5 | 0.5 |
| Purified water | balance | balance | balance | balance | balance | balance |
| Total | 100.0 | 100.0 | 100.0 | 100.0 | 100.0 | 100.0 |

TABLE 5

| | Toothpastes | | | | | |
|---|---|---|---|---|---|---|
| | Example 25 | Example 26 | Example 27 | Example 28 | Example 29 | Example 30 |
| Hydroxyapatite | 20.0 | 20.0 | 20.0 | 20.0 | 20.0 | 20.0 |
| Potassium nitrate | 2.5 | 2.5 | 5.0 | 7.5 | 10.0 | 10.0 |
| Calcium monohydrogen phosphatedihydrate | 0.5 | 25.0 | 20.0 | 5.0 | 0.5 | 25.0 |
| Glycerin | 20.0 | 20.0 | 20.0 | 20.0 | 20.0 | 20.0 |
| Polyethylene glycol | 3.0 | 3.0 | 3.0 | 3.0 | 3.0 | 3.0 |
| Sodium lauryl sulfate | 1.0 | 1.0 | 1.0 | 1.0 | 1.0 | 1.0 |
| Xanthan gum | 0.5 | 0.5 | 0.5 | 0.5 | 0.5 | 0.5 |
| Hydroxyethyl cellulose | 0.5 | 0.5 | 0.5 | 0.5 | 0.5 | 0.5 |
| Menthol | 0.5 | 0.5 | 0.5 | 0.5 | 0.5 | 0.5 |
| Purified water | balance | balance | balance | balance | balance | balance |
| Total | 100.0 | 100.0 | 100.0 | 100.0 | 100.0 | 100.0 |

TABLE 6

| | Toothpastes | | | | | |
|---|---|---|---|---|---|---|
| | Comparative Example 2 | Comparative Example 3 | Comparative Example 4 | Comparative Example 5 | Comparative Example 6 | Comparative Example 7 |
| Hydroxyapatite | — | 0.5 | 1.0 | 5.0 | 10.0 | 20.0 |
| Potassium nitrate | — | — | — | — | — | — |
| Calcium monohydrogen phosphate dihydrate | — | — | — | — | — | — |
| Glycerin | 20.0 | 20.0 | 20.0 | 20.0 | 20.0 | 20.0 |
| Polyethylene glycol | 3.0 | 3.0 | 3.0 | 3.0 | 3.0 | 3.0 |
| Sodium lauryl sulfate | 1.0 | 1.0 | 1.0 | 1.0 | 1.0 | 1.0 |
| Xanthan gum | 0.5 | 0.5 | 0.5 | 0.5 | 0.5 | 0.5 |
| Hydroxyethyl cellulose | 0.5 | 0.5 | 0.5 | 0.5 | 0.5 | 0.5 |
| Menthol | 0.5 | 0.5 | 0.5 | 0.5 | 0.5 | 0.5 |
| Purified water | balance | balance | balance | balance | balance | balance |
| Total | 100.0 | 100.0 | 100.0 | 100.0 | 100.0 | 100.0 |

TABLE 7

| Toothpastes | Comparative Example 8 | Comparative Example 9 | Comparative Example 10 | Comparative Example 11 |
|---|---|---|---|---|
| Hydroxyapatite | — | — | — | — |
| Potassium nitrate | 2.5 | 5.0 | 7.5 | 10.0 |
| Calcium monohydrogen phosphate dihydrate | — | — | — | — |
| Glycerin | 20.0 | 20.0 | 20.0 | 20.0 |
| Polyethylene glycol | 3.0 | 3.0 | 3.0 | 3.0 |
| Sodium lauryl sulfate | 1.0 | 1.0 | 1.0 | 1.0 |
| Xanthan gum | 0.5 | 0.5 | 0.5 | 0.5 |
| Hydroxyethyl cellulose | 0.5 | 0.5 | 0.5 | 0.5 |
| Menthol | 0.5 | 0.5 | 0.5 | 0.5 |
| Purified water | balance | balance | balance | balance |
| Total | 100.0 | 100.0 | 100.0 | 100.0 |

TABLE 8

| Toothpastes | Comparative Example 12 | Comparative Example 13 | Comparative Example 14 | Comparative Example 15 | Comparative Example 16 | Comparative Example 17 |
|---|---|---|---|---|---|---|
| Hydroxyapatite | — | — | — | — | — | — |
| Potassium nitrate | — | — | — | — | — | — |
| Calcium monohydrogen phosphate dihydrate | 0.5 | 1.0 | 5.0 | 10.0 | 20.0 | 25.0 |
| Glycerin | 20.0 | 20.0 | 20.0 | 20.0 | 20.0 | 20.0 |
| Polyethylene glycol | 3.0 | 3.0 | 3.0 | 3.0 | 3.0 | 3.0 |
| Sodium lauryl sulfate | 1.0 | 1.0 | 1.0 | 1.0 | 1.0 | 1.0 |
| Xanthan gum | 0.5 | 0.5 | 0.5 | 0.5 | 0.5 | 0.5 |
| Hydroxyethyl cellulose | 0.5 | 0.5 | 0.5 | 0.5 | 0.5 | 0.5 |
| Menthol | 0.5 | 0.5 | 0.5 | 0.5 | 0.5 | 0.5 |
| Purified water | balance | balance | balance | balance | balance | balance |
| Total | 100.0 | 100.0 | 100.0 | 100.0 | 100.0 | 100.0 |

TABLE 9

| Toothpastes | Comparative Example 18 | Comparative Example 19 | Comparative Example 20 | Comparative Example 21 | Comparative Example 22 | Comparative Example 23 |
|---|---|---|---|---|---|---|
| Hydroxyapatite | 0.5 | 0.5 | — | 0.5 | 0.5 | — |
| Potassium nitrate | — | 2.5 | 2.5 | — | 10.0 | 10.0 |
| Calcium monohydrogen phosphate dihydrate | 0.5 | — | 0.5 | 25.0 | — | 25.0 |
| Glycerin | 20.0 | 20.0 | 20.0 | 20.0 | 20.0 | 20.0 |
| Polyethylene glycol | 3.0 | 3.0 | 3.0 | 3.0 | 3.0 | 3.0 |
| Sodium lauryl sulfate | 1.0 | 1.0 | 1.0 | 1.0 | 1.0 | 1.0 |
| Xanthan gum | 0.5 | 0.5 | 0.5 | 0.5 | 0.5 | 0.5 |
| Hydroxyethyl cellulose | 0.5 | 0.5 | 0.5 | 0.5 | 0.5 | 0.5 |
| Menthol | 0.5 | 0.5 | 0.5 | 0.5 | 0.5 | 0.5 |
| Purified water | balance | balance | balance | balance | balance | balance |
| Total | 100.0 | 100.0 | 100.0 | 100.0 | 100.0 | 100.0 |

TABLE 10

| Toothpastes | Comparative Example 24 | Comparative Example 25 | Comparative Example 26 | Comparative Example 27 | Comparative Example 28 | Comparative Example 29 |
|---|---|---|---|---|---|---|
| Hydroxyapatite | 1.0 | 1.0 | — | 1.0 | 1.0 | — |
| Potassium nitrate | — | 5.0 | 5.0 | — | 2.5 | 2.5 |
| Calcium monohydrogen phosphate dihydrate | 5.0 | — | 5.0 | 25.0 | — | 25.0 |
| Glycerin | 20.0 | 20.0 | 20.0 | 20.0 | 20.0 | 20.0 |
| Polyethylene glycol | 3.0 | 3.0 | 3.0 | 3.0 | 3.0 | 3.0 |

TABLE 10-continued

| | Toothpastes | | | | | |
|---|---|---|---|---|---|---|
| | Comparative Example 24 | Comparative Example 25 | Comparative Example 26 | Comparative Example 27 | Comparative Example 28 | Comparative Example 29 |
| Sodium lauryl sulfate | 1.0 | 1.0 | 1.0 | 1.0 | 1.0 | 1.0 |
| Xanthan gum | 0.5 | 0.5 | 0.5 | 0.5 | 0.5 | 0.5 |
| Hydroxyethyl cellulose | 0.5 | 0.5 | 0.5 | 0.5 | 0.5 | 0.5 |
| Menthol | 0.5 | 0.5 | 0.5 | 0.5 | 0.5 | 0.5 |
| Purified water | balance | balance | balance | balance | balance | balance |
| Total | 100.0 | 100.0 | 100.0 | 100.0 | 100.0 | 100.0 |

TABLE 11

| | Toothpastes | | | | | |
|---|---|---|---|---|---|---|
| | Comparative Example 30 | Comparative Example 31 | Comparative Example 32 | Comparative Example 33 | Comparative Example 34 | Comparative Example 35 |
| Hydroxyapatite | 5.0 | 5.0 | — | 5.0 | 5.0 | — |
| Potassium nitrate | — | 5.0 | 5.0 | — | 10.0 | 10.0 |
| Calcium monohydrogen phosphate dihydrate | 10.0 | — | 10.0 | 0.5 | — | 0.5 |
| Glycerin | 20.0 | 20.0 | 20.0 | 20.0 | 20.0 | 20.0 |
| Polyethylene glycol | 3.0 | 3.0 | 3.0 | 3.0 | 3.0 | 3.0 |
| Sodium lauryl sulfate | 1.0 | 1.0 | 1.0 | 1.0 | 1.0 | 1.0 |
| Xanthan gum | 0.5 | 0.5 | 0.5 | 0.5 | 0.5 | 0.5 |
| Hydroxyethyl cellulose | 0.5 | 0.5 | 0.5 | 0.5 | 0.5 | 0.5 |
| Menthol | 0.5 | 0.5 | 0.5 | 0.5 | 0.5 | 0.5 |
| Purified water | balance | balance | balance | balance | balance | balance |
| Total | 100.0 | 100.0 | 100.0 | 100.0 | 100.0 | 100.0 |

TABLE 12

| | Toothpastes | | | | | |
|---|---|---|---|---|---|---|
| | Comparative Example 36 | Comparative Example 37 | Comparative Example 38 | Comparative Example 39 | Comparative Example 40 | Comparative Example 41 |
| Hydroxyapatite | 10.0 | 10.0 | — | 10.0 | 10.0 | — |
| Potassium nitrate | — | 7.5 | 7.5 | — | 5.0 | 5.0 |
| Calcium monohydrogen phosphate dihydrate | 20.0 | — | 20.0 | 1.0 | — | 1.0 |
| Glycerin | 20.0 | 20.0 | 20.0 | 20.0 | 20.0 | 20.0 |
| Polyethylene glycol | 3.0 | 3.0 | 3.0 | 3.0 | 3.0 | 3.0 |
| Sodium lauryl sulfate | 1.0 | 1.0 | 1.0 | 1.0 | 1.0 | 1.0 |
| Xanthan gum | 0.5 | 0.5 | 0.5 | 0.5 | 0.5 | 0.5 |
| Hydroxyethyl cellulose | 0.5 | 0.5 | 0.5 | 0.5 | 0.5 | 0.5 |
| Menthol | 0.5 | 0.5 | 0.5 | 0.5 | 0.5 | 0.5 |
| Purified water | balance | balance | balance | balance | balance | balance |
| Total | 100.0 | 100.0 | 100.0 | 100.0 | 100.0 | 100.0 |

TABLE 13

| | Toothpastes | | | | |
|---|---|---|---|---|---|
| | Comparative Example 42 | Comparative Example 43 | Comparative Example 44 | Comparative Example 45 | Comparative Example 46 |
| Hydroxyapatite | 20.0 | 20.0 | 20.0 | 20.0 | — |
| Potassium nitrate | — | 10.0 | — | 7.5 | 7.5 |
| Calcium monohydrogen phosphate dihydrate | 25.0 | — | 5.0 | — | 5.0 |
| Glycerin | 20.0 | 20.0 | 20.0 | 20.0 | 20.0 |
| Polyethylene glycol | 3.0 | 3.0 | 3.0 | 3.0 | 3.0 |
| Sodium lauryl sulfate | 1.0 | 1.0 | 1.0 | 1.0 | 1.0 |

TABLE 13-continued

Toothpastes

| | Comparative Example 42 | Comparative Example 43 | Comparative Example 44 | Comparative Example 45 | Comparative Example 46 |
|---|---|---|---|---|---|
| Xanthan gum | 0.5 | 0.5 | 0.5 | 0.5 | 0.5 |
| Hydroxyethyl cellulose | 0.5 | 0.5 | 0.5 | 0.5 | 0.5 |
| Menthol | 0.5 | 0.5 | 0.5 | 0.5 | 0.5 |
| Purified water | balance | balance | balance | balance | balance |
| Total | 100.0 | 100.0 | 100.0 | 100.0 | 100.0 |

TABLE 14

Mouthwashes

| | Example 31 | Example 32 | Example 33 | Comparative Example 47 | Comparative Example 48 | Comparative Example 49 |
|---|---|---|---|---|---|---|
| Hydroxyapatite | 0.5 | 0.5 | 0.5 | 0.5 | — | — |
| Potassium nitrate | 2.5 | 5.0 | 10.0 | — | 10.0 | — |
| Calcium monohydrogen phosphate dihydrate | 0.5 | 0.5 | 0.5 | — | — | 0.5 |
| Ethyl alcohol | 10.0 | 10.0 | 10.0 | 10.0 | 10.0 | 10.0 |
| Sodium lauryl sulfate | 1.0 | 1.0 | 1.0 | 1.0 | 1.0 | 1.0 |
| Glycerin | 10.0 | 10.0 | 10.0 | 10.0 | 10.0 | 10.0 |
| Menthol | 0.4 | 0.4 | 0.4 | 0.4 | 0.4 | 0.4 |
| Purified water | balance | balance | balance | balance | balance | balance |
| Total | 100.0 | 100.0 | 100.0 | 100.0 | 100.0 | 100.0 |

TABLE 15

Mouthwashes

| | Comparative Example 50 | Comparative Example 51 | Comparative Example 52 | Comparative Example 53 | Comparative Example 54 | Comparative Example 55 | Comparative Example 56 |
|---|---|---|---|---|---|---|---|
| Hydroxyapatite | 0.5 | 0.5 | 0.5 | 0.5 | — | — | — |
| Potassium nitrate | 2.5 | 5.0 | 10.0 | — | 2.5 | 5.0 | 10.0 |
| Calcium monohydrogen phosphate dihydrate | — | — | — | 0.5 | 0.5 | 0.5 | 0.5 |
| Ethyl alcohol | 10.0 | 10.0 | 10.0 | 10.0 | 10.0 | 10.0 | 10.0 |
| Sodium lauryl sulfate | 1.0 | 1.0 | 1.0 | 1.0 | 1.0 | 1.0 | 1.0 |
| Glycerin | 10.0 | 10.0 | 10.0 | 10.0 | 10.0 | 10.0 | 10.0 |
| Menthol | 0.4 | 0.4 | 0.4 | 0.4 | 0.4 | 0.4 | 0.4 |
| Purified water | balance | balance | balance | balance | balance | balance | balance |
| Total | 100.0 | 100.0 | 100.0 | 100.0 | 100.0 | 100.0 | 100.0 |

TABLE 16

Dentinal tubule-occluding agents

| | Example 34 | Example 35 | Example 36 | Example 37 | Example 38 | Example 39 |
|---|---|---|---|---|---|---|
| Hydroxyapatite | 1.0 | 5.0 | 5.0 | 5.0 | 5.0 | 5.0 |
| Potassium nitrate | 2.5 | 5.0 | 10.0 | 2.5 | 5.0 | 7.5 |
| Calcium monohydrogen phosphate dihydrate | 1.0 | 0.5 | 5.0 | 10.0 | 15.0 | 20.0 |
| Polyethylene glycol | 5.0 | 5.0 | 5.0 | 5.0 | 5.0 | 5.0 |
| Purified water | balance | balance | balance | balance | balance | balance |
| Total | 100.0 | 100.0 | 100.0 | 100.0 | 100.0 | 100.0 |

TABLE 17

Dentinal tubule-occluding agents

| | Example 40 | Example 41 | Example 42 | Example 43 | Example 44 |
|---|---|---|---|---|---|
| Hydroxyapatite | 5.0 | 10.0 | 10.0 | 10.0 | 10.0 |
| Potassium nitrate | 10.0 | 2.5 | 5.0 | 7.5 | 10.0 |
| Calcium monohydrogen phosphate dihydrate | 20.0 | 20.0 | 25.0 | 25.0 | 25.0 |
| Polyethylene glycol | 5.0 | 5.0 | 5.0 | 5.0 | 5.0 |
| Purified water | balance | balance | balance | balance | balance |
| Total | 100.0 | 100.0 | 100.0 | 100.0 | 100.0 |

TABLE 18

Dentinal tubule-occluding agents

| | Example 45 | Example 46 | Example 47 | Example 48 | Example 49 |
|---|---|---|---|---|---|
| Hydroxyapatite | 15.0 | 15.0 | 15.0 | 15.0 | 20.0 |
| Potassium nitrate | 2.5 | 5.0 | 7.5 | 10.0 | 2.5 |
| Calcium monohydrogen phosphate dihydrate | 20.0 | 10.0 | 5.0 | 0.5 | 20.0 |
| Polyethylene glycol | 5.0 | 5.0 | 5.0 | 5.0 | 5.0 |
| Purified water | balance | balance | balance | balance | balance |
| Total | 100.0 | 100.0 | 100.0 | 100.0 | 100.0 |

TABLE 19

Dentinal tubule-occluding agents

| | Comparative Example 57 | Comparative Example 58 | Comparative Example 59 | Comparative Example 60 |
|---|---|---|---|---|
| Hydroxyapatite | 1.0 | 5.0 | 10.0 | 20.0 |
| Potassium nitrate | — | — | — | — |
| Calcium monohydrogen phosphate dihydrate | | | | |
| Polyethylene glycol | 5.0 | 5.0 | 5.0 | 5.0 |
| Purified water | balance | balance | balance | balance |
| Total | 100.0 | 100.0 | 100.0 | 100.0 |

TABLE 20

Dentinal tubule-occluding agents

| | Comparative Example 61 | Comparative Example 62 | Comparative Example 63 | Comparative Example 64 |
|---|---|---|---|---|
| Hydroxyapatite | — | — | — | — |
| Potassium nitrate | 2.5 | 5.0 | 7.5 | 10.0 |
| Calcium monohydrogen phosphate dihydrate | — | — | — | — |
| Polyethylene glycol | 5.0 | 5.0 | 5.0 | 5.0 |
| Purified water | balance | balance | balance | balance |
| Total | 100.0 | 100.0 | 100.0 | 100.0 |

TABLE 21

Dentinal tubule-occluding agents

| | Comparative Example 65 | Comparative Example 66 | Comparative Example 67 | Comparative Example 68 | Comparative Example 69 | Comparative Example 70 | Comparative Example 71 |
|---|---|---|---|---|---|---|---|
| Hydroxyapatite | — | — | — | — | — | — | — |
| Potassium nitrate | — | — | — | — | — | — | — |
| Calcium monohydrogen phosphate dihydrate | 0.5 | 1.0 | 5.0 | 10.0 | 15.0 | 20.0 | 25.0 |
| Polyethylene glycol | 5.0 | 5.0 | 5.0 | 5.0 | 5.0 | 5.0 | 5.0 |
| Purified water | balance | balance | balance | balance | balance | balance | balance |
| Total | 100.0 | 100.0 | 100.0 | 100.0 | 100.0 | 100.0 | 100.0 |

TABLE 22

Dentinal tubule-occluding agents

| | Comparative Example 72 | Comparative Example 73 | Comparative Example 74 |
|---|---|---|---|
| Hydroxyapatite | 1.0 | 1.0 | — |
| Potassium nitrate | 2.5 | — | 2.5 |
| Calcium monohydrogen phosphate dihydrate | — | 1.0 | 1.0 |
| Polyethylene glycol | 5.0 | 5.0 | 5.0 |
| Purified water | balance | balance | balance |
| Total | 100.0 | 100.0 | 100.0 |

TABLE 23

Dentinal tubule-occluding agents

| | Comparative Example 75 | Comparative Example 76 | Comparative Example 77 | Comparative Example 78 | Comparative Example 79 | Comparative Example 80 |
|---|---|---|---|---|---|---|
| Hydroxyapatite | 5.0 | 5.0 | — | 5.0 | 5.0 | — |
| Potassium nitrate | 5.0 | — | 5.0 | 10.0 | — | 10.0 |
| Calcium monohydrogen phosphate dihydrate | — | 15.0 | 15.0 | — | 20.0 | 20.0 |
| Polyethylene glycol | 5.0 | 5.0 | 5.0 | 5.0 | 5.0 | 5.0 |
| Purified water | balance | balance | balance | balance | balance | balance |
| Total | 100.0 | 100.0 | 100.0 | 100.0 | 100.0 | 100.0 |

TABLE 24

Dentinal tubule-occluding agents

| | Comparative Example 81 | Comparative Example 82 | Comparative Example 83 |
|---|---|---|---|
| Hydroxyapatite | 10.0 | 10.0 | — |
| Potassium nitrate | 10.0 | — | 10.0 |
| Calcium monohydrogen phosphate dihydrate | — | 25.0 | 25.0 |
| Polyethylene glycol | 5.0 | 5.0 | 5.0 |
| Purified water | balance | balance | balance |
| Total | 100.0 | 100.0 | 100.0 |

TABLE 25

Dentinal tubule-occluding agents

| | Comparative Example 84 | Comparative Example 85 | Comparative Example 86 | Comparative Example 87 | Comparative Example 88 | Comparative Example 89 |
|---|---|---|---|---|---|---|
| Hydroxyapatite | 15.0 | 15.0 | — | 15.0 | 15.0 | — |
| Potassium nitrate | 2.5 | — | 2.5 | — | 5.0 | 5.0 |
| Calcium monohydrogen phosphate dihydrate | — | 20.0 | 20.0 | 10.0 | — | 10.0 |
| Polyethylene glycol | 5.0 | 5.0 | 5.0 | 5.0 | 5.0 | 5.0 |
| Purified water | balance | balance | balance | balance | balance | balance |
| Total | 100.0 | 100.0 | 100.0 | 20.0 | 100.0 | 100.0 |

TABLE 26

Dentinal tubule-occluding agents

| | Comparative Example 90 | Comparative Example 91 | Comparative Example 92 | Comparative Example 93 | Comparative Example 94 | Comparative Example 95 |
|---|---|---|---|---|---|---|
| Hydroxyapatite | 15.0 | 15.0 | — | 15.0 | 15.0 | — |
| Potassium nitrate | 7.5 | — | 7.5 | — | 10.0 | 10.0 |
| Calcium monohydrogen phosphate dihydrate | — | 5.0 | 5.0 | 0.5 | — | 0.5 |
| Polyethylene glycol | 5.0 | 5.0 | 5.0 | 5.0 | 5.0 | 5.0 |
| Purified water | balance | balance | balance | balance | balance | balance |
| Total | 100.0 | 100.0 | 100.0 | 20.0 | 100.0 | 100.0 |

TABLE 27

| | Dentinal tubule-occluding agents | | |
|---|---|---|---|
| | Comparative Example 96 | Comparative Example 97 | Comparative Example 98 |
| Hydroxyapatite | 20.0 | 20.0 | — |
| Potassium nitrate | — | 2.5 | 2.5 |
| Calcium monohydrogen phosphate dihydrate | 20.0 | — | 20.0 |
| Polyethylene glycol | 5.0 | 5.0 | 5.0 |
| Purified water | balance | balance | balance |
| Total | 20.0 | 100.0 | 100.0 |

Dentinal Tubule Occlusion Test

A healthy human evulsion tooth was used to cut the tooth into sections in such a manner that dentin and dentinal tubules were exposed. The resulting sections were polished at a thickness of about 500 μm and were subjected to ultrasonic cleaning. Next, 25 g of each of the dentifrices, mouthwashes, and dentinal tubule-occluding agents of the Examples and Comparative Examples was adjusted with distilled water to have a volume of 40 mL. The resulting solution was used as a test solution. Then, the sections whose portions other than the test surface had been masked were soaked in the test solution at 37° C. for 9 min per day. This soaking treatment was conducted for 5 days.

After the soaking, the treatment surface of dentin was observed with a field emission scanning electron microscope FE-SEM (S-4500, manufactured by Hitachi, Ltd.) (magnification: 1,500× or 2,000×). FIGS. 1 to 7 show electron micrographs of the untreated surface and the treated surface of the dentin of a tooth after the soaking test. FIGS. 1 to 7 clearly demonstrate that the sections treated using an oral composition according to the present invention exhibited occlusion of dentinal tubules of a tooth.

Figure 8:
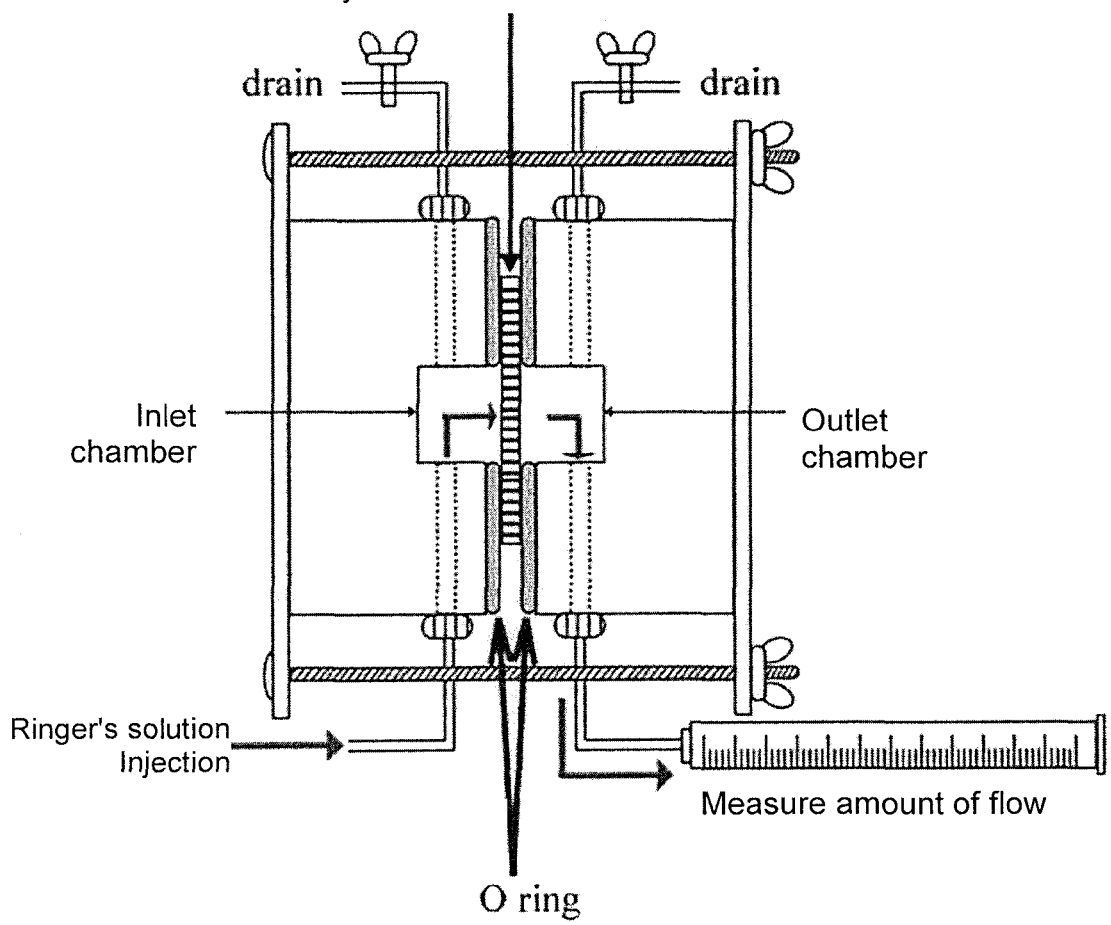
FIG. 8 illustrates a split chamber device used for a test for liquid permeation through dentinal tubules.

In addition, a test for liquid permeation through dentinal tubules was conducted. The test for liquid permeation through dentinal tubules was conducted according to the Pashley's protocol disclosed in "O. W. Reeder et al., J. Dent. Res., 57, (2); 187-193, 1978." A split chamber device shown in FIG. 8 was prepared and put into practice. A dentin section was interposed between an inlet chamber and an outlet chamber of the above device. Then, the test solution was placed in the inlet chamber to treat the dentin surface. In addition, a Ringer's solution was injected using pressure in the inlet chamber before and after the treatment. By measuring the amount of flow through the outlet chamber, the liquid permeation through dentinal tubules was evaluated.

As a Comparative Example for the dentifrice, a commercially available dentifrice (containing aluminum lactate known to have an ability to occlude dentinal tubules of a tooth), which was sold and advertised to have a hypersensitivity-inhibiting effect, was used (in Comparative Example 1).

The effect of inhibiting liquid permeation through dentinal tubules of each test solution was determined as follows: first, a difference between the amount of flow of the Ringer's solution before and that after the treatment was determined; and a liquid permeation inhibition rate of the dentinal tubules was then calculated in percent units by using the following equation.

Occlusion rate (%)=(Amount of flow before treatment−Amount of flow after treatment)/(Amount of flow before treatment)×100.

Table 28 shows the results.

TABLE 28

| Toothpastes | Example/Comparative Example | | | | | | |
|---|---|---|---|---|---|---|---|
| Toothpastes | Example/Comparative Example | Example 1 | Example 2 | Example 3 | Example 4 | Example 5 | Example 6 |
| | Dentinal tubule occlusion rate (%) | 29.6 | 49 | 39.7 | 48.9 | 34.5 | 53.7 |
| Toothpastes | Example/Comparative Example | Example 7 | Example 8 | Example 9 | Example 10 | Example 11 | Example 12 |
| | Dentinal tubule occlusion rate (%) | 40.5 | 59.9 | 51.3 | 55.1 | 46.4 | 65.1 |
| Toothpastes | Example/Comparative Example | Example 13 | Example 14 | Example 15 | Example 16 | Example 17 | Example 18 |
| | Dentinal tubule occlusion rate (%) | 51.9 | 71 | 65.1 | 67.8 | 56.3 | 75.2 |
| Toothpastes | Example/Comparative Example | Example 19 | Example 20 | Example 21 | Example 22 | Example 23 | Example 24 |
| | Dentinal tubule occlusion rate (%) | 63.6 | 83 | 70.6 | 85.7 | 69.2 | 87.7 |
| Toothpastes | Example/Comparative Example | Example 25 | Example 26 | Example 27 | Example 28 | Example 29 | Example 30 |
| | Dentinal tubule occlusion rate (%) | 90.6 | 100 | 100 | 100 | 95.8 | 100 |
| Toothpastes | Example/Comparative Example | Comp. Ex. 1 | Comp. Ex. 2 | Comp. Ex. 3 | Comp. Ex. 4 | Comp. Ex. 5 | Comp. Ex. 6 | Comp. Ex. 7 |
| | Dentinal tubule occlusion rate (%) | 51.4 | 0 | 6.4 | 12.6 | 18.1 | 25.6 | 42.3 |
| Toothpastes | Example/Comparative Example | Comp. Ex. 8 | Comp. Ex. 9 | Comp. Ex. 10 | Comp. Ex. 11 | | |
| | Dentinal tubule occlusion rate (%) | 0 | 0 | 0 | 0 | | |
| Toothpastes | Example/Comparative Example | Comp. Ex. 12 | Comp. Ex. 13 | Comp. Ex. 14 | Comp. Ex. 15 | Comp. Ex. 16 | Comp. Ex. 17 |
| | Dentinal tubule occlusion rate (%) | 3.5 | 6.5 | 10.7 | 14 | 19.3 | 22.1 |
| Toothpastes | Example/Comparative Example | Comp. Ex. 18 | Comp. Ex. 19 | Comp. Ex. 20 | Comp. Ex. 21 | Comp. Ex. 22 | Comp. Ex. 23 |
| | Dentinal tubule occlusion rate (%) | 9.3 | 6.4 | 3.1 | 28.7 | 6.4 | 21.9 |

TABLE 28-continued

| Toothpastes | Example/Comparative Example | Comp. Ex. 24 | Comp. Ex. 25 | Comp. Ex. 26 | Comp. Ex. 27 | Comp. Ex. 28 | Comp. Ex. 29 | |
|---|---|---|---|---|---|---|---|---|
| | Dentinal tubule occlusion rate (%) | 23.9 | 12.8 | 10.8 | 34.6 | 12.2 | 22.5 | |
| Toothpastes | Example/Comparative Example | Comp. Ex. 30 | Comp. Ex. 31 | Comp. Ex. 32 | Comp. Ex. 33 | Comp. Ex. 34 | Comp. Ex. 35 | |
| | Dentinal tubule occlusion rate (%) | 32.6 | 18.2 | 14.4 | 21.9 | 18.7 | 3.2 | |
| Toothpastes | Example/Comparative Example | Comp. Ex. 36 | Comp. Ex. 37 | Comp. Ex. 38 | Comp. Ex. 39 | Comp. Ex. 40 | Comp. Ex. 41 | |
| | Dentinal tubule occlusion rate (%) | 45.7 | 25.8 | 19.2 | 32.4 | 25.5 | 6.8 | |
| Toothpastes | Example/Comparative Example | Comp. Ex. 42 | Comp. Ex. 43 | Comp. Ex. 44 | Comp. Ex. 45 | Comp. Ex. 46 | | |
| | Dentinal tubule occlusion rate (%) | 64.6 | 42 | 53.4 | 42.6 | 10.1 | | |
| Mouthwashes | Example/Comparative Example | Example 31 | Example 32 | Example 33 | Comp. Ex. 47 | Comp. Ex. 48 | Comp. Ex. 49 | |
| | Dentinal tubule occlusion rate (%) | 30.4 | 33.3 | 35.3 | 6.5 | 0 | 3.3 | |
| Mouthwashes | Example/Comparative Example | Comp. Ex. 50 | Comp. Ex. 51 | Comp. Ex. 52 | Comp. Ex. 53 | Comp. Ex. 54 | Comp. Ex. 55 | Comp. Ex. 56 |
| | Dentinal tubule occlusion rate (%) | 6.6 | 7.1 | 6.9 | 10.6 | 3.8 | 3 | 3.9 |
| Dentinal tubule-occluding agents | Example/Comparative Example | Example 34 | Example 35 | Example 36 | Example 37 | Example 38 | Example 39 | |
| | Dentinal tubule occlusion rate (%) | 46.5 | 56.3 | 66 | 63.7 | 69.9 | 74.8 | |
| Dentinal tubule-occluding agents | Example/Comparative Example | Example 40 | Example 41 | Example 42 | Example 43 | Example 44 | | |
| | Dentinal tubule occlusion rate (%) | 75 | 82.3 | 87.5 | 89.9 | 90 | | |
| Dentinal tubule-occluding agents | Example/Comparative Example | Example 45 | Example 46 | Example 47 | Example 48 | Example 49 | | |
| | Dentinal tubule occlusion rate (%) | 95.6 | 93.2 | 91.2 | 84.1 | 100 | | |
| Dentinal tubule-occluding agents | Example/Comparative Example | Comp. Ex. 57 | Comp. Ex. 58 | Comp. Ex. 59 | Comp. Ex. 60 | | | |
| | Dentinal tubule occlusion rate (%) | 14.3 | 19.2 | 26 | 43.7 | | | |
| Dentinal tubule-occluding agents | Example/Comparative Example | Comp. Ex. 61 | Comp. Ex. 62 | Comp. Ex. 63 | Comp. Ex. 64 | | | |
| | Dentinal tubule occlusion rate (%) | 0 | 0 | 0 | 0 | | | |
| Dentinal tubule-occluding agents | Example/Comparative Example | Comp. Ex. 65 | Comp. Ex. 66 | Comp. Ex. 67 | Comp. Ex. 68 | Comp. Ex. 69 | Comp. Ex. 70 | Comp. Ex. 71 |
| | Dentinal tubule occlusion rate (%) | 4.5 | 7.8 | 11.5 | 15.1 | 18.7 | 20.1 | 23.2 |
| Dentinal tubule-occluding agents | Example/Comparative Example | Comp. Ex. 72 | Comp. Ex. 73 | Comp. Ex. 74 | | | | |
| | Dentinal tubule occlusion rate (%) | 14.6 | 20.5 | 7.6 | | | | |
| Dentinal tubule-occluding agents | Example/Comparative Example | Comp. Ex. 75 | Comp. Ex. 76 | Comp. Ex. 77 | Comp. Ex. 78 | Comp. Ex. 79 | Comp. Ex. 80 | |
| | Dentinal tubule occlusion rate (%) | 19.4 | 37.5 | 18.7 | 18.7 | 39.5 | 20.8 | |
| Dentinal tubule-occluding agents | Example/Comparative Example | Comp. Ex. 81 | Comp. Ex. 82 | Comp. Ex. 83 | | | | |
| | Dentinal tubule occlusion rate (%) | 27.3 | 49.4 | 23.6 | | | | |
| Dentinal tubule-occluding agents | Example/Comparative Example | Comp. Ex. 84 | Comp. Ex. 85 | Comp. Ex. 86 | Comp. Ex. 87 | Comp. Ex. 88 | Comp. Ex. 89 | |
| | Dentinal tubule occlusion rate (%) | 35.4 | 54.2 | 21.4 | 49.9 | 34.2 | 14.9 | |
| Dentinal tubule-occluding agents | Example/Comparative Example | Comp. Ex. 90 | Comp. Ex. 91 | Comp. Ex. 92 | Comp. Ex. 93 | Comp. Ex. 94 | Comp. Ex. 95 | |
| | Dentinal tubule occlusion rate (%) | 34.9 | 46 | 11.8 | 38.2 | 35.9 | 3.4 | |
| Dentinal tubule-occluding agents | Example/Comparative Example | Comp. Ex. 96 | Comp. Ex. 97 | Comp. Ex. 98 | | | | |
| | Dentinal tubule occlusion rate (%) | 63.6 | 42.7 | 20.1 | | | | |

As demonstrated in Comparative Examples 3 to 7 and 12 to 17, etc., hydroxyapatite and calcium monohydrogen phosphate dihydrate each singly had an ability to occlude dentinal tubules of a tooth. As the amount blended increased, the occlusion rate became higher. By contrast, as shown in Comparative Examples 8 to 11, potassium nitrate alone has no ability to occlude dentinal tubules of a tooth.

In addition, Comparative Example 3 was compared with Comparative Examples 19 and 22; Comparative Example 4 was compared with Comparative Examples 25 and 28;

Comparative Example 5 was compared with Comparative Examples 31 and 34; Comparative Example 6 was compared with Comparative Examples 37 and 40; and Comparative Example 7 was compared with Comparative Examples 43 and 45. These comparisons clearly demonstrate that blending potassium nitrate in hydroxyapatite did not change the occlusion rates compared with those when hydroxyapatite alone was used. Hence, no increase in the occlusion was observed. Likewise, Comparative Example 12 was compared with Comparative Example 20; Comparative Example 13 was compared with Comparative Example 41; Comparative Example 14 was compared with Comparative Example 26; Comparative Example 15 was compared with Comparative Example 32; Comparative Example 16 was compared with Comparative Example 38; and Comparative Example 17 was compared with Comparative Examples 23. These comparisons clearly demonstrate that blending potassium nitrate in calcium monohydrogen phosphate dihydrate did not change the occlusion rates compared with those when calcium monohydrogen phosphate dihydrate alone was used. Hence, no increase in the occlusion was observed.

Further, Comparative Example 18 was compared with Comparative Examples 3 and 12; Comparative Example 21 was compared with Comparative Examples 3 and 17; Comparative Example 24 was compared with Comparative Examples 4 and 14; Comparative Example 27 was compared with Comparative Examples 4 and 17; Comparative Example 30 was compared with Comparative Examples 5 and 15; Comparative Example 33 was compared with Comparative Examples 5 and 12; Comparative Example 36 was compared with Comparative Examples 6 and 16; Comparative Example 39 was compared with Comparative Examples 6 and 13; Comparative Example 42 was compared with Comparative Examples 7 and 17; and Comparative Example 44 was compared with Comparative Examples 7 and 14. These comparisons clearly demonstrate that the occlusion rate when both two components of hydroxyapatite and calcium monohydrogen phosphate dihydrate were blended was substantially the same as a total of the occlusion rates when hydroxyapatite and calcium monohydrogen phosphate dihydrate each singly were blended. Hence, a combination of these components does not cause a synergistic occlusion-promoting effect.

By contrast, use of an oral composition containing three components of hydroxyapatite, potassium nitrate, and calcium monohydrogen phosphate dihydrate according to the present invention resulted in the effect of synergistically increasing an occlusion rate.

Specifically, for example, Example 1 (occlusion rate: 29.6%) or Example 5 (occlusion rate: 34.5%) was compared with Comparative Example 18 (occlusion rate: 9.3%); Example 2 (occlusion rate: 49.0%) or Example 6 (occlusion rate: 53.7%) was compared with Comparative Example 21 (occlusion rate: 28.7%); Example 9 (occlusion rate: 51.3%) was compared with Comparative Example 24 (occlusion rate: 23.9%); Example 8 (occlusion rate: 59.9%) or Example 12 (occlusion rate: 65.1%) was compared with Comparative Example 27 (occlusion rate: 34.6%); Example 13 (occlusion rate: 51.9%) or Example 17 (occlusion rate: 56.3%) was compared with Comparative Example 33 (occlusion rate: 21.9%); Example 21 (occlusion rate: 70.6%) was compared with Comparative Example 39 (occlusion rate: 32.4%); Example 22 (occlusion rate: 85.7%) was compared with Comparative Example 36 (occlusion rate: 45.7%); Example 28 (occlusion rate: 100%) was compared with Comparative Example 44 (occlusion rate: 53.4%); and Example 26 (occlusion rate: 100%) or Example 30 (occlusion rate: 100%) was compared with Comparative Example 42 (occlusion rate: 64.6%). These comparisons clearly demonstrate a synergistic effect obtained by using a combination of the three components.

INDUSTRIAL APPLICABILITY

An oral composition according to the present invention has a quite excellent inhibitory hypersensitivity and its industrial usefulness is high.

The invention claimed is:

1. A method for suppressing hypersensitivity, comprising contacting an oral composition comprising 0.5 to 20% by weight of hydroxyapatite having an average particle size of 0.01 to 10 μm, 2.5 to 10% by weight of potassium nitrate, and 0.5 to 25% by weight of calcium monohydrogen phosphate dihydrate to dentin of a tooth in an oral cavity of a subject in need of increasing an ability to occlude dentinal tubules of a tooth.

* * * * *